(12) United States Patent
Rosenberg et al.

(10) Patent No.: US 8,135,458 B1
(45) Date of Patent: Mar. 13, 2012

(54) SYSTEM AND METHOD FOR IN VIVO SENSOR RECALIBRATION

(75) Inventors: Stuart Rosenberg, Castaic, CA (US); Wenbo Hou, Lancaster, CA (US)

(73) Assignee: Pacesetter, Inc., Sylmar, CA (US)

( * ) Notice: Subject to any disclaimer, the term of this patent is extended or adjusted under 35 U.S.C. 154(b) by 1237 days.

(21) Appl. No.: 11/844,131

(22) Filed: Aug. 23, 2007

(51) Int. Cl.
*A61B 5/05* (2006.01)
*A61B 5/02* (2006.01)
*A61B 5/103* (2006.01)
*A61B 5/117* (2006.01)

(52) U.S. Cl. .................. 600/547; 600/486; 600/587

(58) Field of Classification Search .................. 600/300, 600/485, 486, 487, 488, 547, 561, 587, 593
See application file for complete search history.

(56) References Cited

U.S. PATENT DOCUMENTS

| 6,188,927 B1 | 2/2001 | Lu et al. |
| 6,387,048 B1 | 5/2002 | Schulman et al. |
| 2009/0054793 A1* | 2/2009 | Nunez et al. .................. 600/485 |

FOREIGN PATENT DOCUMENTS

WO 2006023786 A2 3/2006
\* cited by examiner

*Primary Examiner* — Max Hindenburg
*Assistant Examiner* — Adam Eiseman (57) ABSTRACT

A method of in vivo sensor recalibration includes implanting a sensor at an implantation site in a living body; taking a sensor reading with the implanted sensor; taking a first electrical reading across biological material adjacent the implanted sensor; taking a second electrical reading across biological material adjacent the implanted sensor subsequent in time to the taking of the first electrical reading; comparing the first electrical reading with the second electrical reading; and recalibrating the sensor based on the comparison of the first electrical reading to the second electrical reading.

17 Claims, 5 Drawing Sheets

SYSTEM AND METHOD FOR IN VIVO SENSOR RECALIBRATION

FIELD OF THE INVENTION

The present invention relates to medical sensors and methods of operating such sensors. More specifically, the present invention relates to implantable medical sensors and methods of recalibrating such sensors in vivo.

BACKGROUND OF THE INVENTION

The translation of several physiologic sensor technologies from acute laboratory use to chronic implantable use has been hampered to a large degree by chronic drift due to the accumulation of biological material over the sensor. For example, pressure sensors are mounted on catheters with a diaphragm protecting the strain gage element from the blood pool. Acute thrombus formation or long-term fibrotic growth alters the coupling between the blood pressure and the diaphragm deformation, causing a loss in the fidelity of the pressure measurement.

Optical sensors measure reflectance and absorbance of specific wavelengths by the blood to determine the hematocrit, oxygen saturation or glucose levels. Acute thrombus formation or long-term fibrotic growth attenuates some of the emitted light, causing an erroneous measurement.

There is a need in the art for a system that recalibrates sensors in vivo to account for the accumulation of biological material over the sensor when implanted chronically. There is also a need in the art for a method of recalibrating chronically implanted sensors in vivo.

SUMMARY

One aspect of the invention relates to a method of in vivo sensor recalibration. The method includes implanting a sensor at an implantation site in a living body; taking a sensor reading with the implanted sensor; taking a first electrical reading across biological material adjacent the implanted sensor; taking a second electrical reading across biological material adjacent the implanted sensor subsequent in time to the taking of the first electrical reading; comparing the first electrical reading with the second electrical reading; and recalibrating the sensor based on the comparison of the first electrical reading to the second electrical reading.

Another aspect of the invention relates to employing a sensor implanted in a living body. The method includes taking an electrical measurement across biological material adjacent the sensor; and using the electrical measurement to make a determination regarding the biological material.

Another method of in vivo sensor recalibration includes passing an electrical current through biological material adjacent an implanted sensor to obtain a reading regarding impedance and/or conductance of the biological material; using a first characteristic of the impedance and/or conductance reading to determine a first characteristic of the biological material and a second characteristic of the of the impedance and/or conductance reading to determine a second characteristic of the biological material.

The invention also relates to a sensor system that can be recalibrated in response to the accumulation of biological material presenting a risk of interfering with the ability of the sensor system to accurately sense a condition within a patient. The system includes an implantable sensor, an electrode and a processor. The sensor senses the condition within the patient. The electrode is adjacent the sensor. The processor is in communication with the sensor and electrode. The electrode takes an electrical measurement across the biological material. The processor uses the electrical measurement to make a determination regarding the biological material.

While multiple embodiments are disclosed, still other embodiments of the present invention will become apparent to those skilled in the art from the following detailed description, which shows and describes illustrative embodiments of the invention. As will be realized, the invention is capable of modifications in various aspects, all without departing from the spirit and scope of the present invention. Accordingly, the drawings and detailed description are to be regarded as illustrative in nature and not restrictive.

DETAILED DESCRIPTION

Disclosed herein is a system and method for in vivo recalibration of chronically implanted sensors. In one embodiment, electrical readings are taken over a period of time across biological material adjacent the implanted sensor. The electrical readings are compared to each other and information contained in a database. From the comparisons, the system determines the type of biological material accumulating over the sensor and the extent to which the biological material has accumulated. Upon determining the type of biological material and the extent of the biological material accumulation, the system further determines whether or not the sensor should be recalibrated and, if so, to what extent. If the system determines that the biological material accumulation is excessive, the system can provide a warning as opposed to recalibrating the sensor.

Figure 1:
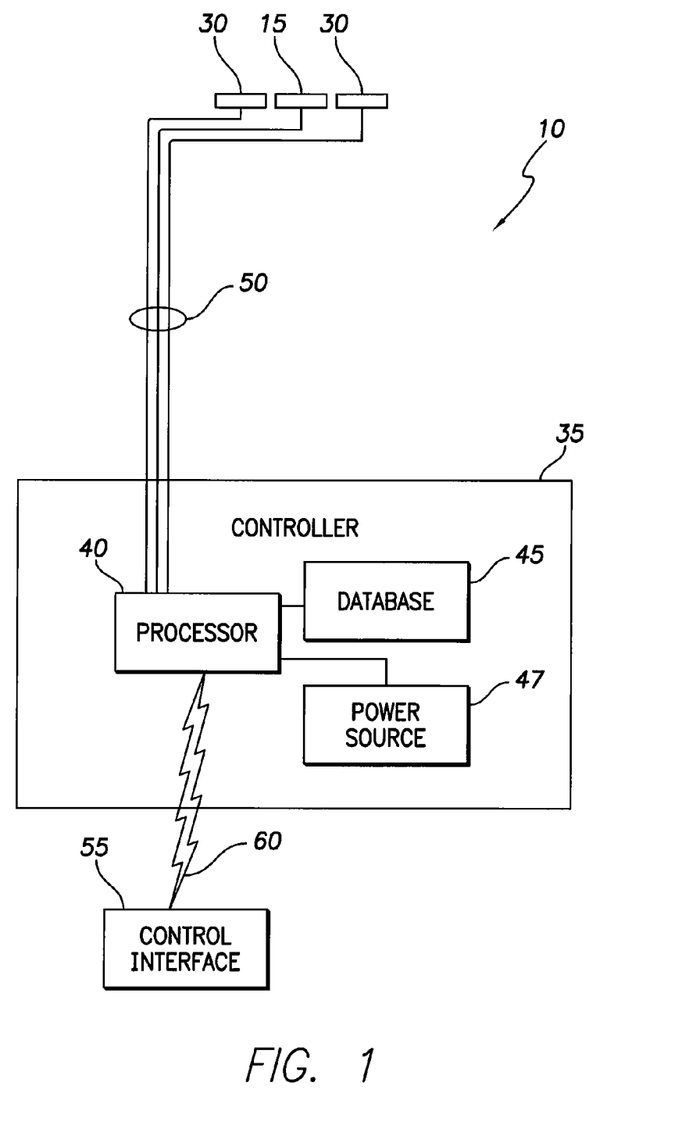
FIG. 1 is a diagrammatic depiction of the system.

For a discussion regarding the system 10, reference is made to FIG. 1, which is a diagrammatic depiction of the system 10. As shown in FIG. 1, in one embodiment, the system 10 includes a sensor 15, one or more electrodes 30, and a controller 35. The controller 35 includes a processor 40, a database 45 and a power source 47, such as a battery 47.

As will be discussed in greater detail below, in one embodiment, the sensor 15 and electrodes 30 are located in close physical proximity to each other such that the electrodes 30 will be in electrical contact with biological material 20 accumulating over the sensor 15. The sensor 15 and electrodes 30 are in electrical communication with the processor 40 via hardwire and/or wireless communication pathways 50. The processor 40 is also in electrical communication with the database 45 via similar pathways. The power source 47 powers the controller 35, sensor 15 and electrodes 30.

In one embodiment, the system 10 further includes a control interface 55. A person, for example, a physician, can use the control interface 55 to communicate with the system 10, for example, input commands and/or data into the system 10 and/or receive information from the system. The control interface 55 is in electrical communication with the processor 40 via electrical pathways 60, which, depending on the embodiment, may be hardwired and/or wireless.

In one embodiment, the sensor 15, electrodes 30 and controller 35 are implanted in a patient, and the controller interface 55 is located outside the patient. In such an embodiment, the controller interface 55 preferably employs a wireless electrical pathway 60 to communicate with the controller 35.

Figure 2:
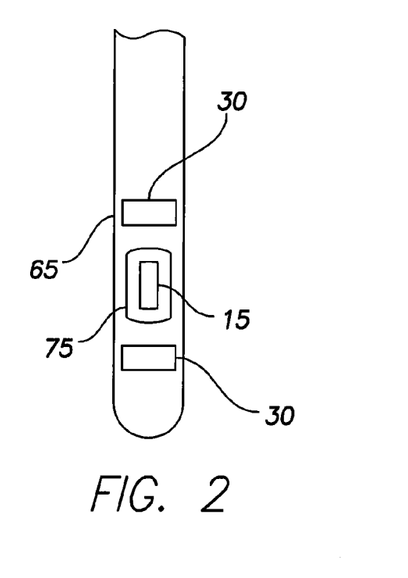
FIG. 2 is a top view of a substrate or body on which the electrodes and sensor are located or carried.
Figure 3:
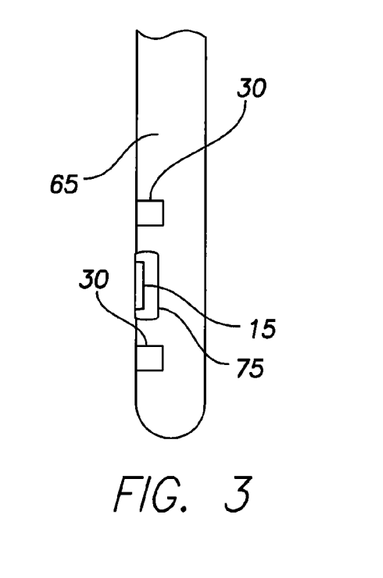
FIG. 3 is a side view of the body depicted in FIG. 2.
Figure 4:
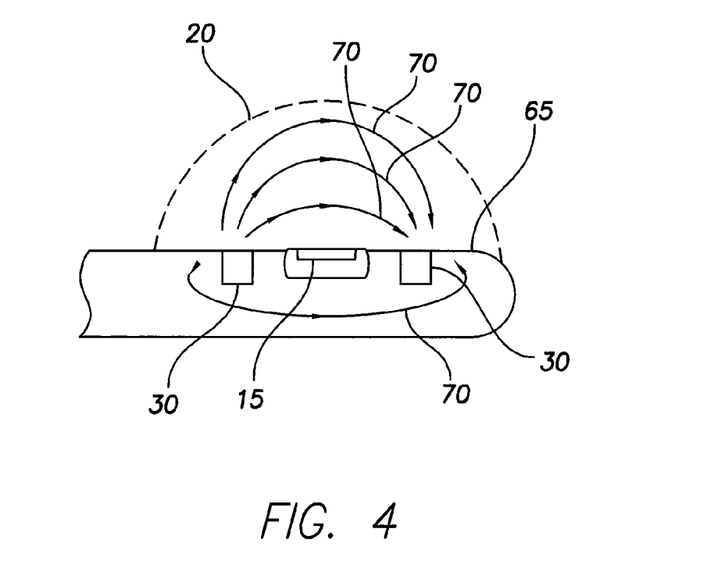
FIG. 4 is another side view of the body depicting current pathways between the electrodes.

For a discussion regarding location of the electrodes 30 relative to the sensor 15, reference is made to FIGS. 2-4. FIG. 2 is a top view of a substrate or body 65 on which the electrodes 30 and sensor 15 are located or carried. FIG. 3 is a side view of the body 65 depicted in FIG. 2. FIG. 4 is another side view of the body 65 depicting current pathways 70 between the electrodes 30.

As shown in FIGS. 2 and 3, in one embodiment, the system further includes a substrate or body 65 on which the sensor 15 and electrodes 30 are mounted or at least carried. In one embodiment, the body 65 simply serves as a substrate for supporting the sensor 15 and electrodes 30 in close proximity to each other at an implantation site within a patient. The body 65 may be a medical device such as an implantable medical lead, a catheter, a sheath, a patch, a "can" (i.e., the case of a pulse generator or other medical electronics package), etc. The portion of the body 65 carrying the sensor 15 and electrodes 30 is implanted at an implantation site within a patient for a permanent or semi-permanent period (e.g., months, years, lifetime). Alternatively, the portion of the body 65 carrying the sensor 15 and electrodes 30 may be routed to a treatment or test site within a patient and remains there for a temporary period (e.g., minutes, hours, days, weeks or months).

In one embodiment, the sensor 15 is a physiological sensor such as a pressure sensor, an optical sensor, a mechanical sensor/strain gage, a chemical sensor, a temperature sensor, a pH sensor, an electrical sensor, an accelerometer, or any other type of physiological sensor. For some embodiments, the sensor 15 will be enclosed via an enclosure 75, wherein the enclosure is in direct contact with blood.

In one configuration, the sensor 15 is of the strain-gage-type pressure sensor. An enclosure 75 such as a thin diaphragm extends over the pressure sensor and transfers blood pressure to the strain-gage of the pressure sensor.

In another configuration, the sensor 15 is an LED-type optical sensor and is used to determine levels of oxygenation, glucose, carbon dioxide, nitric oxide, metabolic byproducts (e.g. urea, amino acids, or other nitrogen wastes), hematocrit, electrolytes, etc. The optical sensor 15 can also be used to determine clarity of fluids such as, for example, lymph fluid, cerebrospinal fluid, etc. Checking the clarity of a fluid can be used, for example, in detecting infection as with a spinal tap.

An enclosure 75 such as a glass, ceramic or polymer window extends over the optical sensor. Light of specific wavelengths passes through the window from an emitter into the blood pool where the light is partially scattered, absorbed, and reflected back through the same window or another similar window.

As indicated in FIGS. 2-3, the electrodes 30 are located in close proximity to the sensor 15. Consequently, as depicted in FIG. 4, current pathways 70 can pass through biological material 20 (e.g., blood, thrombus, myocardial or other body tissue, fibrosis, etc.) accumulating over the sensor 15 and interfering with the sensor's performance.

In one embodiment, the electrodes 30 are a bipolar pair of electrodes. Each electrode 30 is the same size order or slightly smaller than conventional pacing ring electrodes. One electrode 30 is immediately proximal of the sensor 15 and the other electrode is immediately distal of the sensor.

In other embodiments, the electrodes 30 may be of other sizes, polar arrangements, and/or located in other configurations relative to the sensor 15. For example, the electrodes 30 can be configured in a unipolar or multi-polar configuration, a bipolar split ring, or a linear array.

As can be understood from FIG. 4, an electrical signal 70 may be applied between the electrodes 30 to take an electrical reading across the biological material 20 accumulating over the sensor 15. The electrical reading can be a measure of impedance Z or conductance G as calculated according to Ohm's Law (V=IZ or V=I/G, wherein V is voltage, I is current, Z is impedance, and G is conductance).

The electrical signal 70 applied between the electrodes 30 may be a low-amplitude current with a current density that is below the threshold to capture tissue. Alternatively, a small potential may be applied across the electrodes 30. The impedance or conductance of the biological material 20 is then found, for example by Ohm's Law or other calculation or measurement. Changes in impedance or conductance over time can be used to determine the type of the biological material 20 and the extent to which the biological material 20 has accumulated over the sensor 15.

Figure 5A:
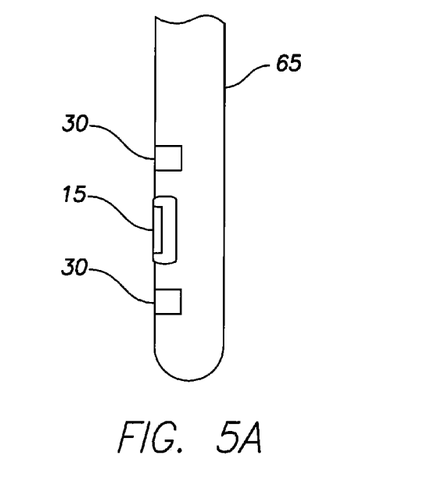
FIG. 5A is generally the same view depicted in FIG. 3, wherein no biological material has accumulated about the sensor.
Figure 5B:
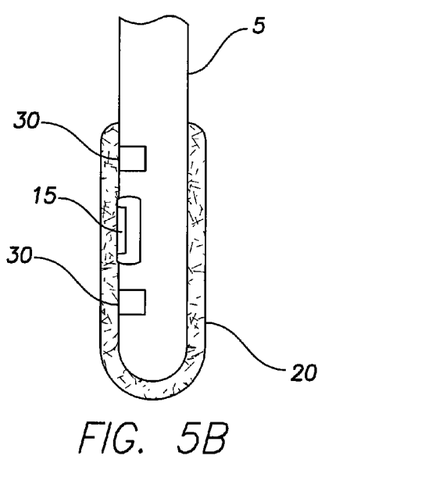
FIG. 5B is the same view depicted in FIG. 5A, except biological material has begun to accumulate about the sensor.
Figure 5C:
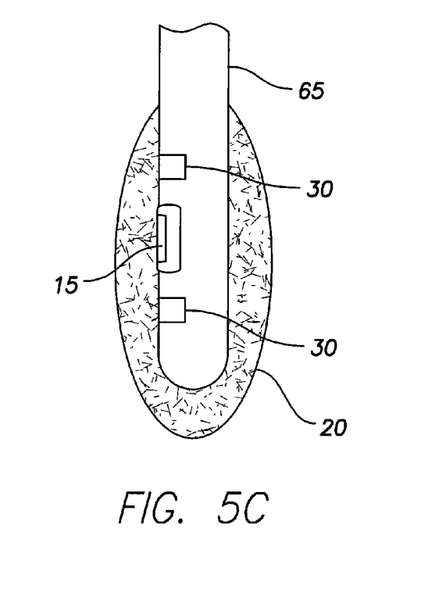
FIG. 5C is the same view depicted in FIG. 5B, except with a greater amount of biological material accumulation about the sensor.
Figure 5D:
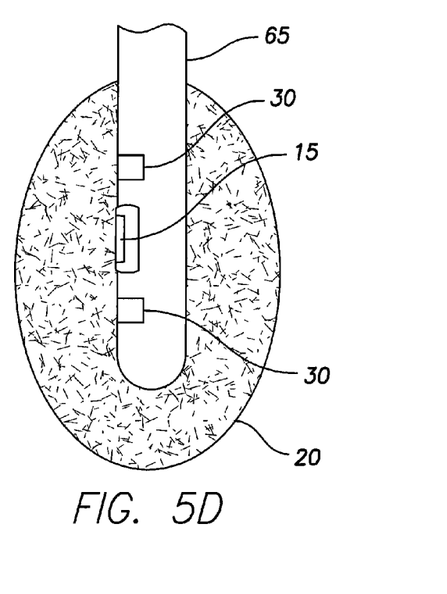
FIG. 5D is the same view depicted in FIG. 5C, except with a greater amount of biological material accumulation about the sensor.
Figure 6:
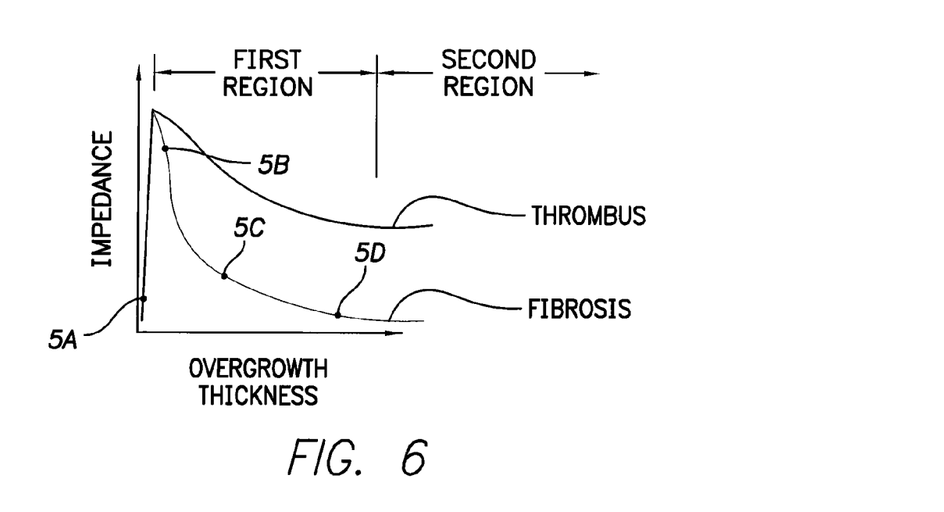
FIG. 6 is a graph depicting the relationship between impedance and overgrowth thickness of the biological material accumulation of FIGS. 5A-5D.
Figure 7A:
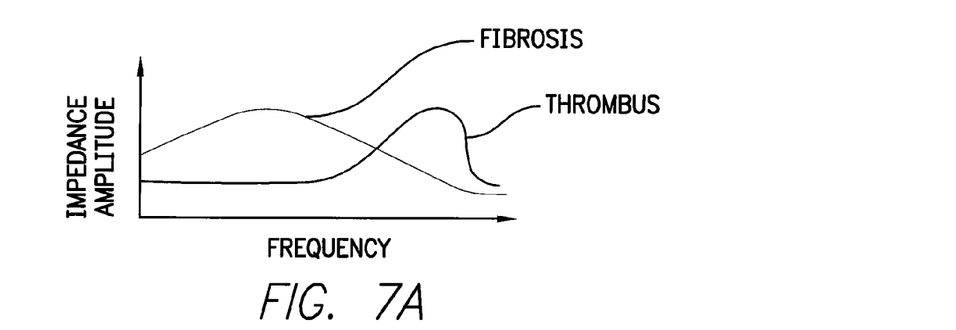
FIGS. 7A and 7B is a graph depicting the relationships between biological material type and impedance amplitude and impedance phase.
Figure 7B:
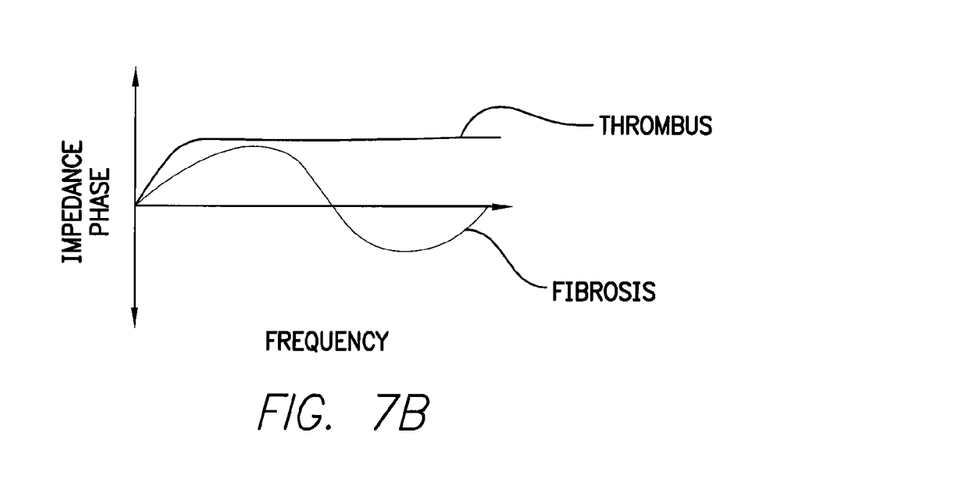

For a discussion regarding the operation of the system 10, reference is made to FIGS. 1 and 4 and FIGS. 5A-6. FIGS. 5A-5D illustrate a progressive accumulation of a biological material 20, such as fibrosis, thrombus, etc., about the sensor 15. FIG. 6 is a graph depicting the relationship between impedance and accumulation/overgrowth thickness of the biological material accumulation of FIGS. 5A-5D. FIGS. 7A and 7B are graphs depicting the relationships between biological material type and impedance amplitude and impedance phase.

In one embodiment, the impedance measurement is taken across the biological material 20 under DC conditions. In such an embodiment, for a given biological material 20, including blood, healthy myocardium, thrombus overgrowth, or fibrotic overgrowth, the impedance or resistance of the biological material 20 decreases monotonically, although not linearly, with the amount of biological material accumulated (see FIG. 6). Taken another way, the conductance of the accumulated/overgrown biological material 20 increases with the thickness of the accumulated biological material.

In one embodiment, the impedance measurement is taken across the biological material 20 under AC conditions. In such an embodiment, for a given frequency, the measured response (e.g., the phase and amplitude of the impedance measurement) would be characteristic and different for various biological materials (see FIGS. 7A and 7B, which are taken over the same frequency range). Taken another way, the biological material's conductance measured at a particular frequency can yield information about the type of biological material 20 accumulating. For example, the measured response at different frequencies would allow a thrombus to be distinguished from fibrosis or another inflammatory response.

In one embodiment, impedance (or conductance) measurements can be taken under more than one condition (e.g., via AC at several frequencies, DC, or at various output levels of DC) to profile both the type and thickness of the accumulated biological material 20. Biologic tissues are generally nonlinear in many aspects, and such nonlinearity may extend to impedance characteristics with respect to current or voltage applied. That is, across a moderate range of applied current, all of which may be sub-threshold, one may see a broad range of impedance, and such response may be characteristic of a given type of tissue. Preliminary testing in a lab setting can provide a thorough understanding of the response to a range of frequencies for various types and thickness of biological material. The response information obtained via the lab setting can be stored in the database 45 for comparison to response information obtained via actual in vivo impedance (or conductance) measurements.

Just as various biological materials 20 have characteristic impedances (and conductances), various biological materials also have differing mechanical and optical properties. Preliminary testing in a lab setting can determine for various biological materials 20 (e.g., fibrosis, thrombus, etc.) a priori stiffness information, such as the Young's Modulus for biological material, as well as optical information, such as admittance, absorbance, or reflectance of the biological material at various wavelengths used in sensor applications. The stiffness and optical information obtained via the lab setting can be stored in the database 45. Once impedance (or conductance) measurements taken across the biological material 20 via the electrodes 30 are used to determine the type and thickness of the accumulated biological material, the stored stiffness and optical information can be used by the processor 40 to determine the proper recalibration, if any, of the sensor 15 based on the type and thickness of the biological material accumulating over the sensor.

As can be understood from FIGS. 5A-6, in one embodiment, the impedance (conductance) will decrease (increase) monotonically and asymptotically with increasing overgrowth thickness. Thus, at a sufficiently thick layer, any increase in thickness no longer appreciably reduces impedance (increases conductance).

FIG. 5A depicts a condition wherein no biological material 20 has overgrown or accumulated over the sensor 15. As shown at 5A in FIG. 6, the impedance corresponding to the condition depicted in FIG. 5A is very low.

FIG. 5B depicts a condition wherein a thin layer of biological material 20 (e.g., fibrosis) has overgrown or accumulated over the sensor 15. As shown at 5B in FIG. 6, the impedance corresponding to the condition depicted in FIG. 5B is very high.

FIGS. 5C and 5D depict conditions with increasingly thick layers of biological material 20 (e.g., fibrosis) overgrown or accumulated over the sensor 15. As shown at 5C and 5D in FIG. 6, as the thickness of the layer of biological material 20 (e.g., fibrosis) increases, the impedance decreases. However, once the biological material 20 reaches a sufficiently great thickness (e.g., as indicated at 5D in FIG. 6), any increase in thickness no longer appreciably reduces impedance. Thus, the impedance-thickness relationship depicted in FIG. 6 includes two regions, a "first region" wherein increases in overgrowth thickness result in an appreciable decrease in impedance, and a "second region" wherein increases in overgrowth thickness result in no appreciable decrease in impedance (i.e., a substantially horizontal area of the impedance-overgrowth thickness graph illustrated in FIG. 6).

In one embodiment, the system 10 addresses the two "regions" differently. In regions such as the "first region" where impedance is dependent on thickness, the result of measuring impedance may be used to estimate the overgrowth thickness and subsequently recalibrate the sensor appropriately. However, in asymptotic regions such as the "second region" where impedance is independent of thickness, the sensor is not recalibrated and an appropriate warning is issued. In one embodiment, the warning is issued via telemetry at a subsequent follow-up, alerting the physician that the sensor 15 is largely encapsulated and may not provide high-fidelity data or that the patient has a particularly large thrombus formation and should receive hemolytic intervention.

The preceding discussion of FIGS. 5A-6 is made in the context of the biological material 20 being fibrosis. However, it can be seen in FIG. 6 that a similar curve and outcome occurs where the biological material 20 is thrombus. Similar curves and outcomes occur where the biological material 20 is other biological material, such as blood, myocardial tissue, etc.

The relationships discussed with respect to FIGS. 5A-6 are made in the context of impedance. However, those skilled in the art will readily understand that similar, but inverse, relationships will exist for conductance.

As can be understood from FIGS. 7A and 7B, which are graphical representations of impedance amplitude and phase for different biological materials 20 taken over the same frequency range, in one embodiment, impedance of the biological material 20 does not vary monotonically with frequency. Thus, by characterizing the frequency-dependent impedance of various overgrowth biological materials 20 at a wide range of frequencies in the laboratory, a finite set of specific frequencies may be chosen to distinguish among the biological materials 20 with only a few impedance measurements. Such a feature helps to save time and conserve battery life, particularly when continually monitoring impedance to recalibrate sensor signals.

The relationships discussed with respect to FIGS. 7A-7B are made in the context of impedance. However, those skilled in the art will readily understand that similar, but inverse, relationships will exist for conductance with respect to at least amplitude.

In other embodiments, relationships similar to those depicted in FIGS. 7A-7B can be provided wherein impedance is on the abscissa and current or voltage amplitude is on the ordinate. As with FIGS. 7A-7B, different biologic materials would have difference characteristic nonlinearities, which can be used to identify the biological materials.

As can be understood from FIGS. 5A-5D, where the sensor 15 is a pressure sensor, the stiffness of the overgrown biological material 20 shields the strain gage of the pressure sensor 15 from deformation, reducing the overall signal amplitude and possibly attenuating the higher-frequency response, as biologic materials 20 are inherently viscoelastic. Where the sensor 15 is an optical sensor, the opacity of the overgrown biological material 20 absorbs or reflects differently from the normally surrounding conditions (e.g., blood or fluid). In cases with less than 100% absorbance or less than 100% reflectance, some of the emitted light will still reach the blood pool and be collected by the sensor 15.

Figure 8:
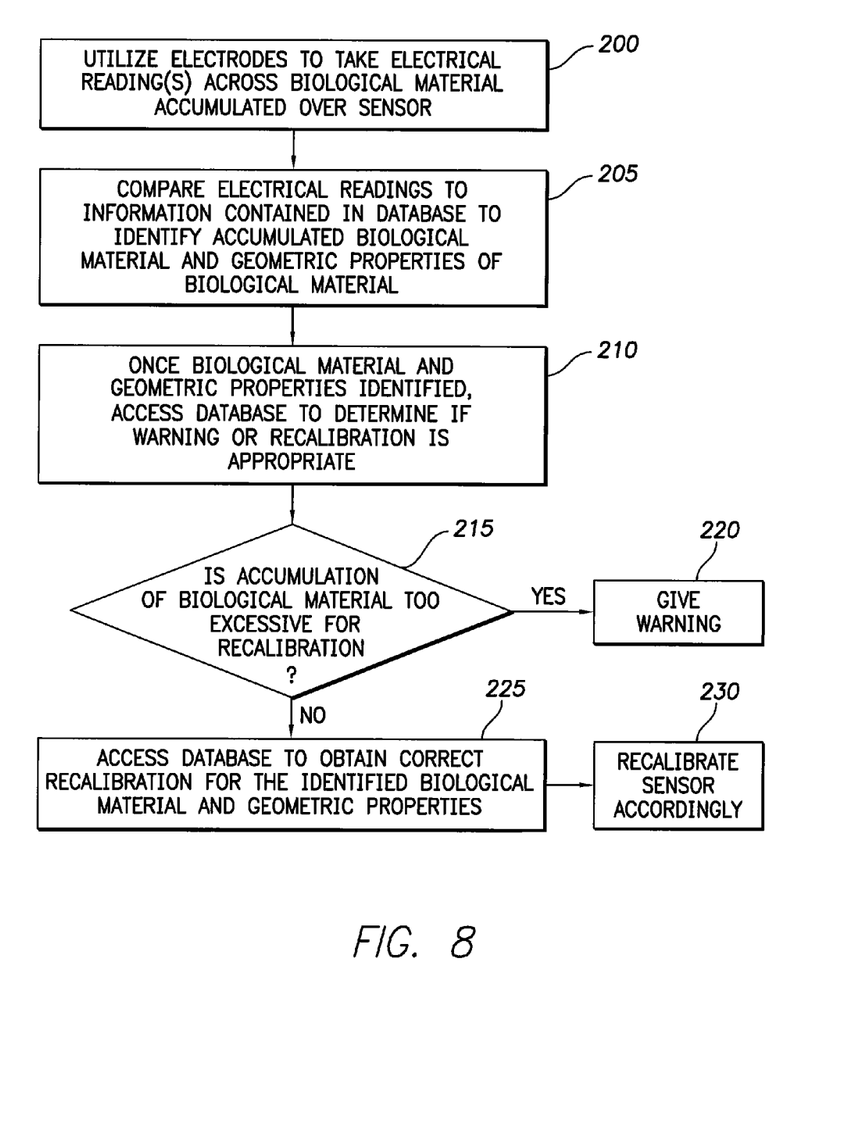
FIG. 8 is a block diagram illustrating one embodiment of a method of recalibrating a sensor.

As can be understood from FIGS. 1, 4, 5A-7B and 8, wherein FIG. 8 is a block diagram illustrating one embodiment of a method of recalibrating a sensor 15, to determine whether to recalibrate the sensor or provide a warning, the system 10 utilizes the electrodes 30 to take a number of electrical readings (e.g., conductance, impedance, and/or resistance) across the accumulated biological material 20 at different frequencies [block 200]. The electrical readings are compared to information contained in a database to identify the accumulated biological material 20 and geometric properties (e.g., the thickness) of the biological material 20 [block 205]. Once the biological material 20 and its geometric properties are identified, the database can again be accessed to determine if a warning or recalibration is warranted [blocks 210 and 215]. If the accumulation of biological material 20 is too excessive for recalibration, a warning is given and no recalibration occurs [block 220]. If the accumulation of biological material 20 is not too excessive for recalibration, then the database 45 is accessed to obtain the correct recalibration for the identified biological material 20 and thickness [block 225]. The processor 40 then recalibrates the sensor 15 accordingly [block 230].

For example, where the sensor 15 is a pressure sensor, the database 45 contains a slope factor for calibrating a pressure signal (e.g., how many mm Hg for each mV). The slope factor is used to determine how to reset the pressure sensor to account for the shielding effect of the identified biological material 20 with the identified thickness.

As another example, where the sensor 15 is an optical sensor, the database 45 contains a slope factor for calibrating a physiologic measure, such as oxygenation or glucose level, that can be reset to account for the additional absorbance and reflectance presented by the accumulated biological material 20.

Although the present invention has been described with reference to preferred embodiments, persons skilled in the art will recognize that changes may be made in form and detail without departing from the spirit and scope of the invention.

What is claimed is:

1. A method of calibrating a sensor implanted in a body, said method comprising:
   taking a plurality of electrical measurements across biological material adjacent a sensor using electrodes;
   providing a processor for performing the following steps:
      using the electrical measurements to make determinations regarding the type of the biological material and the thickness of the biological material;
      based on the type and thickness of the biological material, determining whether the sensor can be recalibrated; and,
      if the sensor can be recalibrated, selecting a recalibration value based on the type and thickness of the biological material.

2. The method of claim 1, wherein the sensor is a pressure sensor.

3. The method of claim 1, wherein the sensor is an optical sensor.

4. The method of claim 1, wherein the plurality of electrical measurements comprises a plurality of electrical measurements at different frequencies, and using the electrical measurements to make the determination regarding the type of the biological material includes comparing the frequency response of the plurality of electrical measurements at different frequencies to information in a database that correlates frequency response to biological material type.

5. The method of claim 4 wherein the plurality of electrical measurements at different frequencies are amplitude measurements.

6. The method of claim 4 wherein the plurality of electrical measurements at different frequencies are phase measurements.

7. The method of claim 4, wherein the plurality of electrical measurements comprises an impedance or conductance magnitude, and using the electrical measurements to make the determination regarding the thickness of the biological material includes comparing the impedance or conductance magnitude to information in a database that correlates impedance or conductance magnitudes and biological material types to biological material thickness.

8. The method of claim 7, wherein determining whether the sensor can be recalibrated comprises comparing the biological material thickness to information in a database that correlates biological material thickness to a first region wherein increases in thickness result in an appreciable decrease in impedance and recalibration is appropriate, and to a second region wherein increases in thickness result in no appreciable decrease in impedance and recalibration is not appropriate.

9. The method of claim 7, wherein selecting a recalibration value based on the type and thickness of the biological material comprises accessing a database having information that correlates biological material type and thickness to recalibration setting.

10. A method of in vivo sensor recalibration, said method comprising:
    passing an electrical current through biological material adjacent an implanted sensor using electrodes to obtain a reading regarding impedance and/or conductance of the biological material;
    providing a processor for performing the following steps:
       using a first characteristic of the impedance and/or conductance reading to determine a type of the biological material and a second characteristic of the impedance and/or conductance reading together with the determined type of biological material to determine a thickness of the biological material; and
       using the determined type of the biological material together with the determined thickness of the biological material to determine whether the sensor can be recalibrated; and,
       if the sensor can be recalibrated, using the determined type of the biological material together with the determined thickness of the biological material to select a recalibration parameter.

11. The method of claim 10, wherein the first characteristic of the impedance and/or conductance reading is frequency response and using the first characteristic comprises comparing the frequency response to a database that correlates frequency responses to biological material types.

12. The method of claim 11, wherein the biological material type is blood, thrombus overgrowth, myocardium, or fibrotic overgrowth.

13. The method of claim 10, wherein the second characteristic of the impedance and/or conductance reading is magnitude and using the second characteristic comprises comparing the magnitude to a database that correlates magnitudes and biological material types to biological material thickness.

14. A sensor system that can be recalibrated in response to the accumulation of biological material presenting a risk of interfering with the ability of the sensor system to accurately sense a condition within a patient, said system comprising:
    an implantable sensor that senses the condition within the patient;
    an electrode adjacent the sensor, the electrode configured to take a plurality of electrical measurements across the biological material;
    a database having information that correlates electrical measurements to biological material type, and that correlates electrical measurements and biological material types to biological material thickness, and that correlates biological material types and biological material thicknesses to recalibration parameters; and a processor in communication with the sensor, the electrode and the database, wherein the processor: uses the electrical measurements to determine the type of biological material; uses the electrical measurements together with the determined type of biological material to determine the thickness of biological material; uses the determined type of biological material together with the determined thickness of biological material to determine whether the sensor can be recalibrated; and, if the sensor can be recalibrated, uses the determined type of biological material together with the determined thickness of biological material to determine a recalibration parameter.

15. The system of claim 14, wherein the electrical measurements comprise one or more of impedance, conductance, and resistance.

16. The system of claim 14, wherein the processor processes the phase of the electrical measurements to determine the type of the biological material.

17. The system of claim 14 wherein the processor processes the amplitude of the electrical measurements to determine the thickness of the biological material.

* * * * *